US00PP12373P2

(12) United States Plant Patent
Machida et al.

(10) Patent No.: US PP12,373 P2
(45) Date of Patent: Jan. 29, 2002

(54) JAPANESE PEAR TREE NAMED 'AKIZUKI'

(75) Inventors: Yutaka Machida, Tsuchiura; Kazuo Kotobuki; Yoshihiko Sato, both of Tsukuba; Kazuyuki Abe, Sagae; Akio Kurihara, Tsuchiura; Tatsushi Ogata, Nagasaki-ken; Toshihiro Saito, Tsukuba; Osami Terai, Nagasaki-ken; Toyohide Nishibata, Nishinomiya; Teruo Kozono, deceased, late of Tsukuba, by Yoshiko Kozono, legal representative; Hiroyuki Fukuda, Hirosaki; Takeshi Kihara, Shimizu; Katsuyuki Suzuki, Tsuchiura, all of (JP)

(73) Assignee: National Institute of Fruit Tree Science, Ministry of Agriculture, Forestry and Fisheries, Tsukuba (JP)

( * ) Notice: Subject to any disclaimer, the term of this patent is extended or adjusted under 35 U.S.C. 154(b) by 0 days.

(21) Appl. No.: 09/526,720

(22) Filed: Mar. 16, 2000

(51) Int. Cl.[7] ..... A01H 5/00
(52) U.S. Cl. ..... Plt./178
(58) Field of Search ..... Plt./178

*Primary Examiner*—Bruce R. Campell
*Assistant Examiner*—A Para
(74) *Attorney, Agent, or Firm*—Armstrong, Westerman, Hattori, McLeland & Naughton, LLP

(57) ABSTRACT

A new and distinct cultivar of russet type Japanese pear tree that has strong tree vigor and a strong resistance to black spot disease. This pear tree bears large size fruit, the harvesting stage of the fruit being mid to late in season after the 'Hosui' cultivar. This pear tree bears large size fruit having excellent quality, such as being highly sweet and weakly acidic.

4 Drawing Sheets

BACKGROUND OF THE INVENTION

The present invention relates to a new and distinct cultivar of Japanese pear tree (*Pyrus pyrifolia*), and particularly to a russet type pear tree forming mid to late season ripening fruits having excellent quality, and having a significantly strong resistance to black spot disease.

In Japan, recent trends in distribution of russet type Japanese pear cultivars leans towards excellent cultivars, known as 'Hosui' (unpatented in the U.S.) and 'Kosui' (unpatented in the U.S.). However, a new excellent variety which can be harvested subsequent to 'Hosui' is required.

ORIGIN AND ASEXUAL REPRODUCTION OF THE VARIETY

The present new variety of Japanese pear tree was a cross-seedling which originated from a crossing between '162-29' (♀) (the seed parent) (unpatented in the U.S.) and 'Kosui' (♂) (the pollen parent). The seed parent '169-29' is a russet type Japanese pear variety having large fruits with excellent quality, ripening slightly late in the season, and having resistance to black spot disease, and was bred by a crossing between 'Niitaka' (unpatented in the U.S.) and 'Hosui'. The crossing between '169-29' and 'Kosui' was carried out in 1985, seeds were obtained, and seedlings from the seeds were planted at a selection field in 1987. The tree bore fruit for the first time in 1990, and the maturation period, resistance to disease and the quality of the fruit satisfied the above-stated purpose. Thus the tree was selected as the first selection in 1991, and subjected to local adaptability tests from 1992 at 34 experimental stations in the main pear growing regions, such as Saitama-ken, Tottori-ken, Chiba-ken, Ibaraki-ken, of Japan, as the strain number 'Pear Tsukuba No. 47'. As a result, this new variety was judged to be a russet type pear variety having good quality and harvestable between 'Hosui' and 'Niitaka', and this new variety of Japanese pear tree was named 'Akizuki' in 1998. The genus and species of the variety is *Pyrus pyrifolia*.

This new and distinct variety of Japanese pear tree 'Akizuki' was asexually reproduced at the National Institute of Fruit Tree Science, Ministry of Agriculture, Forestry and Fisheries (MAFF), at 2-1, Fujimoto, Tsukuba-shi, Ibaraki-ken, Japan, by grafting and the homogeneity and stability thereof were confirmed.

SUMMARY OF THE VARIETY

The following description is based on observation of a 12 year old plant grown by trellis training, with fertilizer applications at a rate of N:P:K =10:10:10 Kg/10 a. The observed plant was the original plant raised from a seedling, as opposed to a plant grafted on a rootstock. This new variety has a strong vigor and light greenish-brown, thick shoots. Bearing of spurs of the variety is average and that of axillary flower buds is few to average, and both less than for 'Kosui', 'Hosui' and 'Niitaka'. Flowering time of the variety is late, the same as 'Kosui', and both the color of the flowers just before opening and that of the opened petals are white. The number of petals of the variety are many, but fewer than for 'Kosui'. The color of unopened anthers is deep yellowish pink, resembling that of 'Kosui'. A fruit bearing tree was obtained after four years of culture in the Ibaraki-ken site. The new variety produces large sized, i.e., about 500 g, larger than 'Hosui' and smaller than 'Niitaka', oblate shaped fruits, having wide breath and medium depth of stalk cavity. Ripening of the variety is 10 days later than that of 'Hosui' and about 1 week earlier than 'Niitaka' in Ibaraki-ken, Japan. Self-compatibility of the variety is low, but neither early fruit dropping nor late fruit dropping are observed, and the fruit setting is good, and thus productivity of immature trees of the variety is considered to be much greater than that of 'Hosui'. Occurrence of heart rot, water core and cracking of the fruits are not observed. The fruit of the new variety is russet type pear having yellowish red brown fruit skin with densely distributed medium sized dots. The ratio of calyx perpetual fruit of the variety is high. The flesh of the variety is white colored, soft, compact and the degree of browning of a cut end thereof is medium. The taste of the flesh is highly sweet, slightly sweeter than that of 'Hosui', and is weakly sour, between 'Kosui' and 'Hosui'. Aroma of the fruit of the variety is less than, but the taste is as excellent, as compared to 'Hosui'.

The new variety is distinguishable from 'Kosui' in having stronger vigor, thicker shoots, lighter color of the shoot; the color of scale leaf of flower bud is reddish brown, the color of flower just before opening is white. The new variety is also distinguishable in having large size fruit, the ratio of calyx perpetual fruit being higher and the harvest season being later. The new variety is distinguishable from 'Hosui' in having lighter colored anthers, later flower blooming term, and in having no water core and spheroidal shaped fruit.

DESCRIPTION OF THE INVENTION

Figure 1:
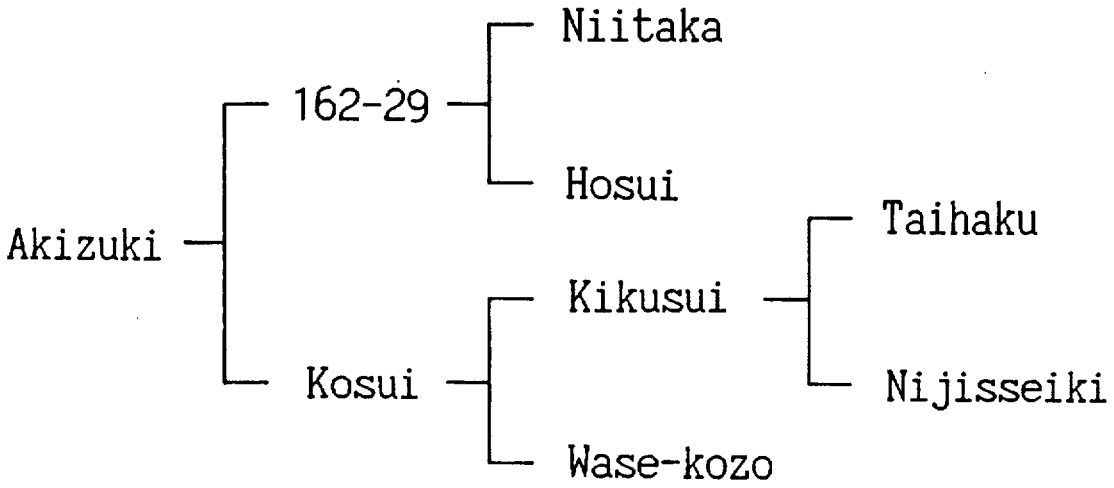
FIG. 1 is the pedigree of the new and distinct variety of Japanese pear 'Akizuki'.
Figure 2:
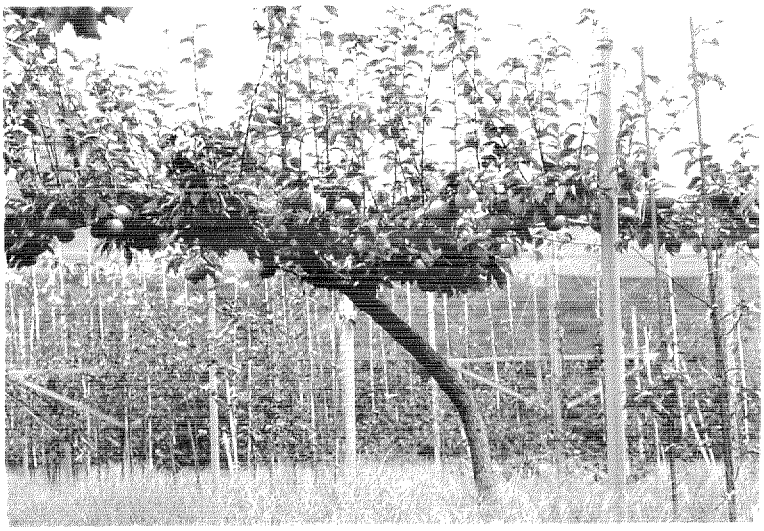
FIG. 2 is a photograph of the tree of the new variety, 'Akizuki', as trained.
Figure 3:
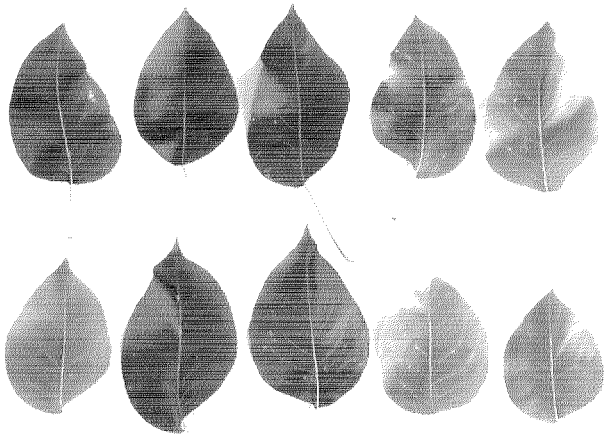
FIG. 3 is a photograph of the adaxial adult leaves of 'Akizuki'.
Figure 4:
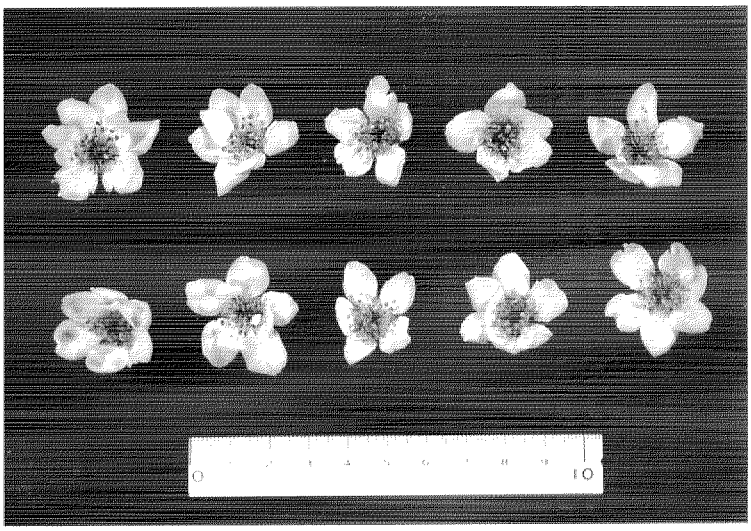
FIG. 4 is a photograph of the flowers of 'Akizuki'.
Figure 5:
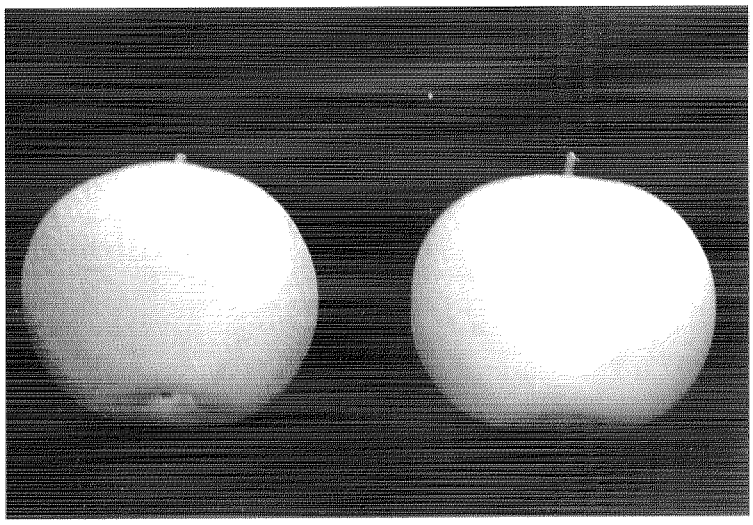
FIG. 5 is a photograph of the side view of fruit of 'Akizuki'.
Figure 6:
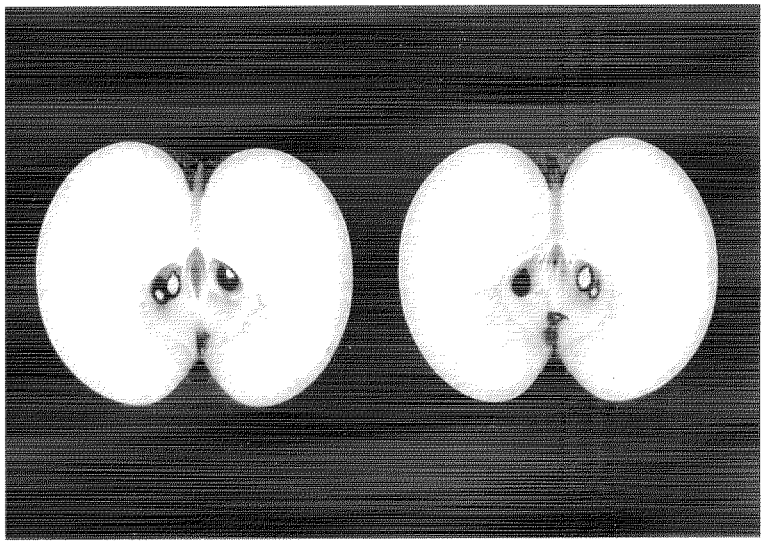
FIG. 6 is a photograph of longitudinal sectional views of fruit of 'Akizuki'.
Figure 7:
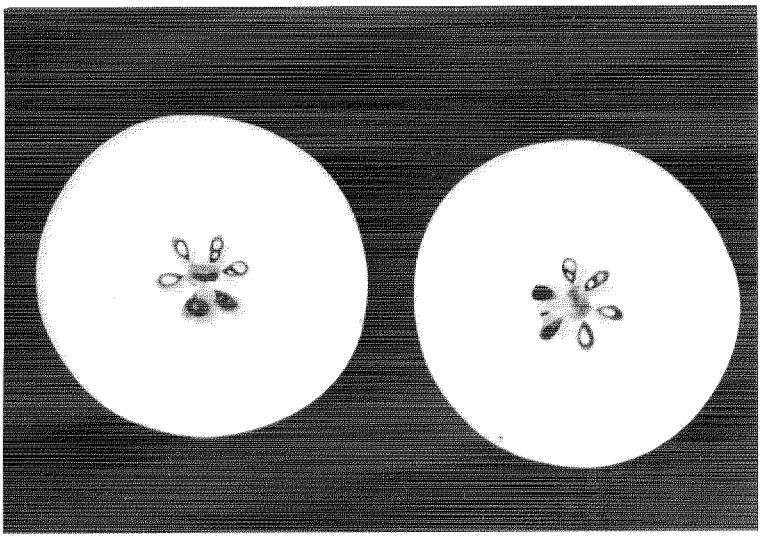
FIG. 7 is a photograph of cross-sectional views of fruit of 'Akizuki'.

The characteristics of the new and distinct cultivar of Japanese pear tree 'Akizuki' are as follows (in the following description, the color-coding is in accordance with The Royal Horticultural Society's R.H.S. Colour Chart, and when a suitable color is not available in the R.H.S. Colour Chart, the color-coding is in accordance with the Japanese Horticultural Society's JHS Color Chart):

Tree:

*Tree diameter.*—4.2 m on 16 year-old tree.

*Trunk diameter.*—17 cm at 20 cm from ground on 16 year-old tree.

*Trunk surface color.*—RHS Greyed-Green 197B.

*Vigor.*—Strong; new shoot growth averaged 125 cm in 1997.

*Branch habit.*—Average: length of shoot is 125 cm, with diameter of 10.2 mm.

*Spurs.*—Medium, in 1999 an average of 8.5 per meter of a branch.

*Number of axillary flower buds.*—Ratio of 28% (i.e., slightly less than average.

*Time of bud break.*—Medium, around April 2 at Ibaraki-ken, Japan.

*Production.*—Average productivity: average of 13.3 Kg produced per plant on six-year old plant, as measured throughout Japan at 34 experimental stations where local adaptability tests were performed.

*Cross-compatibility.*—Cross compatible with 'Kosui', 'Hosui', 'Gold Nijjiseiki' (U.S. Plant Pat. No. 8,529) and 'Niitaka', but incompatible with Chikusui (U.S. Plant Pat. No. 7,758). The tree has low self-compatibility, but fruit setting is high.

Branches (Shoot):

*Length.*—Average, about 125 cm.

*Diameter.*—Thick, about 10.2 mm.

*Length of internode.*—Short, about 3.6 cm.

*Color.*—RHS Grey-Brown 199A.

*Density of pubescence.*—Not sparse, as typical of a *Pirus pyrifolia.*

*Angle between leaf bud and shoot.*—Acute.

*Size of lenticels.*—Average: 1.5 mm in length, 0.6 mm in width.

*Density of lenticels.*—Medium (about 69.1/10 cm length of branch).

Leaves:

*Shape.*—Ovate. Base: Elliptic. Apex: Acute. Margin: Serrulate.

*Size.*—Medium, (11.3 cm long by 7.4 cm wide).

*Color (adult leaves).*—RHS Green 131A for adaxial leaves and RHS Green 133A for abaxial leaves.

*Length of petiole.*—Medium, about 3.3 cm.

*Thickness of petiole.*—Medium, about 2.7 mm.

*Color of young leaves.*—Red brown RHS Red 46A.

*Density of pubescence of young leaves.*—Sparse.

Flowers:

*Flower number in a flower cluster.*—Medium, about 7.9 flowers per cluster.

*Size.*—Medium, the average flower diameter is about 3.0 cm.

*Color.*—JHS White 01, both at early stages of blooming and the opened flower.

*Petals.*—Ovate, shape of apex and base is rotundate, length of 15 mm, width of 11 mm, smooth texture, color of upper and lower surfaces is RHS 155A.

*Notch of petal margin.*—Few, average of 0.4 per petal.

*Number of petals.*—Many, 6.3 per flower on average.

*Sepals.*—5.5 in number on average, triangular, apex shape acute and gradually increasing in width toward base with no pinching in; length of 5.3 mm, width of 4.3 mm; color of upper surface is RHS 144B and color of lower surface is RHS 143C.

*Color of anthers.*—Deep yellowish pink (RHS Red 44D).

*Stigmas.*—5.6 in number on average, length of 6.3 mm, color RHS 155A.

*Number of stamens.*—Slightly more than medium, 26.7 on average.

*Filaments.*—27.6 in number on average, length of 6.1 mm. color RHS 155B.

*Pollen.*—High amount, color is RHS 8A.

*Ovaries.*—5.6 in number on average, length of 1.2 mm, width of 0.9 mm; color RHS 155D.

*Flowering time.*—Late of the season.

*Flowering date and full bloom stage.*—From April 14 to April 21 in 1997. Around April 16th when 70–80% of flowers opened at the Ibaraki Ken, Japan. (Two days earlier than 'Kosui' and two days later than 'Hosui'). The approximate duration of bloom of the new cultivar at Tukuba, National Institute of Fruit Tree Science (Ibaraki-ken, Japan) was from 7 to 10 days.

Fruit:

*Size.*—Large, 510 g on average in 1992.

*Shape.*—Oblate.

*Color of skin (unbagged fruit).*—Yellowish red brown RHS Greyed-Orange 165B.

*Calyx.*—The ratio of calyx perpetual fruit is high. However, quality of calyx deciduous fruits and calyx perpetual fruit is equivalent.

*Size of dots on fruit skin.*—Medium.

*Density of dots on fruit skin.*—High.

*Color of dots on fruit skin.*—RHS Greyed-Orange 164B.

*Color of flesh.*—JHS Yellowish white 2501.

*Flesh.*—Soft and juicy. The firmness is about 4.1 lbs. according to Magness-Tayler's hardness meter index.

*Length of pedicel.*—Medium, about 2.8 cm.

*Thickness of pedicel.*—Medium. about 3.1 mm.

*Color of pedicel.*—RHS Greyed-Orange 165B.

*Color of core.*—JHS Yellowish white 2501.

*Shape of core.*—Short conical.

*Size of core.*—Ratio of transverse diameter of core to transverse diameter of fruit is medium, 38/103 mm.

*Seed cells.*—Many. 5.6 cells per fruit on average.

*Number of seeds.*—11.2 on average, with 8.4 perfect seeds and 2.8 imperfect seeds.

*Size of seeds.*—Medium, about 8.1 mm by 5.8 mm on average.

*Color of seeds.*—RHS Black 202A.

*Shape of seeds.*—Oval.

*Taste.*—Highly sweet, the total sugar content of the fruit juice is about 12.5%, weak in acidity, pH4.97, and no astringency and few aroma.

*Maturity.*—Ripening between medium and late in the season, e.g., from September 16 To September 29, September 22 (peak harvest) at the Ibaraki-ken, Japan in 1997.

*Period from pollination to ripening.*—About 156 days.

*Productivity.*—The production of a 6-year old immature tree of the new cultivar was 13.3 kg/tree.

*Use.*—Suitable for dessert.

*Keeping quality.*—Can be kept for about 14 days at 25° C.

*Resistance to disease.*—Has a strong resistance to black spot disease not slightly susceptibility to pear scab, and no susceptibity to pear canker and physalospora canker.

*Resistance to insects.*—Medium.

*Culture.*—Suitable for outdoor culture. Winter hardiness to temperature even as low as 10° C.

The new variety, 'Akizuki' is cultivated and kept at the National Institute of Fruit Tree Science, MAFF, Japan.

Occurrence of both spurs and axillary flower buds is less than those of 'Hosui' and 'Niitaka', and maintaining of spurs is not so easy. However as the occurrence of branches is high, these problems can be solved by adequate tree training and pruning methods to obtain the necessary amount of flower buds.

As the fruit of the new variety is large, it is necessary to take adequate measures against strong wind, like a typhoon.

The tree of the new cultivar, 'Akizuki' can be conveniently cultivated in all the agricultural districts where a Japanese pear tree is cultivated.

We claim:

1. A new and distinct cultivar of *Pyrus pyrifolia* (russet type Japanese pear) tree, substantially as herein illustrated and described, characterized by strong tree vigor and its ability to produce large size fruit, a harvesting stage of the fruit from mid to late season, said fruit being highly sweet and weakly acidic, and having a significantly strong resistance to black spot disease.

* * * * *

Redigree of 'Akizuki'

2/4

3/4

4/4

UNITED STATES PATENT AND TRADEMARK OFFICE

CERTIFICATE OF CORRECTION

PATENT NO. : PP 12,373 P2
DATED : January 29, 2002
INVENTOR(S) : Machida et al.

It is certified that error appears in the above-identified patent and that said Letters Patent is hereby corrected as shown below:

Title page,
Item [75], Inventors, "Osumi Terai" should be -- Osamu Terai --

Signed and Sealed this

Third Day of September, 2002

*Attest:*

*Attesting Officer*

JAMES E. ROGAN
*Director of the United States Patent and Trademark Office*